(12) United States Patent
Chen et al.

(10) Patent No.: US 7,687,234 B2
(45) Date of Patent: Mar. 30, 2010

(54) CARBON ELECTRODE SURFACE FOR ATTACHMENT OF DNA AND PROTEIN MOLECULES

(75) Inventors: Ting Chen, Cedar Park, TX (US); Xing Yang, San Diego, CA (US); R. Erik Holmlin, San Diego, CA (US)

(73) Assignee: GeneOhm Sciences, Inc., San Diego, CA (US)

( * ) Notice: Subject to any disclaimer, the term of this patent is extended or adjusted under 35 U.S.C. 154(b) by 189 days.

(21) Appl. No.: 11/011,265

(22) Filed: Dec. 13, 2004

(65) Prior Publication Data

US 2006/0008818 A1    Jan. 12, 2006

Related U.S. Application Data

(60) Provisional application No. 60/530,065, filed on Dec. 15, 2003, provisional application No. 60/620,374, filed on Oct. 20, 2004.

(51) Int. Cl.
   *C12Q 1/68*   (2006.01)
   *C12M 1/34*   (2006.01)
   *C12M 3/00*   (2006.01)
   *C01B 31/00*  (2006.01)
   *C01B 31/04*  (2006.01)

(52) U.S. Cl. .................. 435/6; 435/287.1; 435/287.2; 423/414; 423/448

(58) Field of Classification Search ............ 435/6, 435/287.1, 287.2; 423/414, 448
See application file for complete search history.

(56) References Cited

U.S. PATENT DOCUMENTS

| | | | | |
|---|---|---|---|---|
| 3,883,337 A | * | 5/1975 | Helgesson et al. | 65/31 |
| 4,443,652 A | * | 4/1984 | Izu et al. | 136/251 |
| 4,927,462 A | * | 5/1990 | Sugama | 106/724 |
| 5,304,252 A | * | 4/1994 | Condra et al. | 134/2 |
| 5,312,527 A | | 5/1994 | Mikkelsen et al. | |
| 5,391,272 A | | 2/1995 | O'Daly et al. | |
| 5,632,957 A | | 5/1997 | Heller et al. | |
| 5,714,407 A | * | 2/1998 | Maeno et al. | 438/701 |
| 6,124,398 A | * | 9/2000 | Imashiro et al. | 525/61 |

(Continued)

OTHER PUBLICATIONS

Usmani et al, J. Materials Science, vol. 16, pp. 1402-1407 (1981).*

(Continued)

*Primary Examiner*—Robert T. Crow
(74) *Attorney, Agent, or Firm*—Knobbe, Martens, Olson & Bear LLP

(57) ABSTRACT

Methods for conducting an assay to detect nucleic acid hybridization are disclosed. In particular, the fabrication of a carbon electrode suited to nucleic acid hybridization detection is described. In some preferred embodiments, a micro array of carbon electrodes is constructed using photolithography. The final step in the photolithography process involves developing a solder mask with an alkaline solution. The alkaline solution oxidizes the carbon surface producing surface carboxylic acid groups. The surface carboxylic acid groups are reacted with EDC or DCC and NHS to produce NHS esters. Immobilization of NEUTRAVIDIN® onto the electrode surface is effected by reaction with the surface NHS ester groups. A biotinylated probe DNA molecule is then attached to the electrode via binding between the biotin group and the immobilized NEUTRAVIDIN®. The resulting electrode can be used to detect hybridization between the probe DNA and complementary target DNA.

25 Claims, 5 Drawing Sheets

Expose and develop solder mask

U.S. PATENT DOCUMENTS

| | | | |
|---|---|---|---|
| 6,180,346 | B1 | 1/2001 | Thorp et al. |
| 6,207,369 | B1 | 3/2001 | Wohlstadter et al. |
| 6,221,586 | B1 | 4/2001 | Barton et al. |
| 6,458,547 | B1 * | 10/2002 | Bryan et al. .................... 506/9 |
| 2001/0021534 | A1 | 9/2001 | Wohlstadter et al. |
| 2001/0023078 | A1 * | 9/2001 | Bawendi et al. ............ 436/524 |
| 2002/0001799 | A1 | 1/2002 | Heller et al. |
| 2002/0121314 | A1 * | 9/2002 | Tao et al. .................... 148/251 |
| 2003/0151344 | A1 * | 8/2003 | Cheng et al. ................ 313/311 |
| 2004/0086892 | A1 | 5/2004 | Crothers et al. |
| 2004/0086894 | A1 | 5/2004 | Crothers et al. |
| 2004/0086895 | A1 | 5/2004 | Crothers et al. |

OTHER PUBLICATIONS

Definition of "dielectric" provided by the online dictionary at merriam-webster.com.*

Defintion of "coat" provided by the online dictionary at merriam-webster.com.*

Defintion of "insulator" provided by the online dictionary at yourdictionary.com.*

A.B. Steel et al., "Electrochemical Quantitation of DNA Immobilized on Gold," *Anal. Chem.* 70:4670-77 (1998).

* cited by examiner

Additive Process

Form electrode

Form dielectric layer

Subtractive Process

Form electrode

Coat dielectric layer

Define dielectric layer

Carbon Electrode Array Fabrication

Define copper traces

Screen-print carbon electrodes

Coat solder mask

Expose and develop solder mask

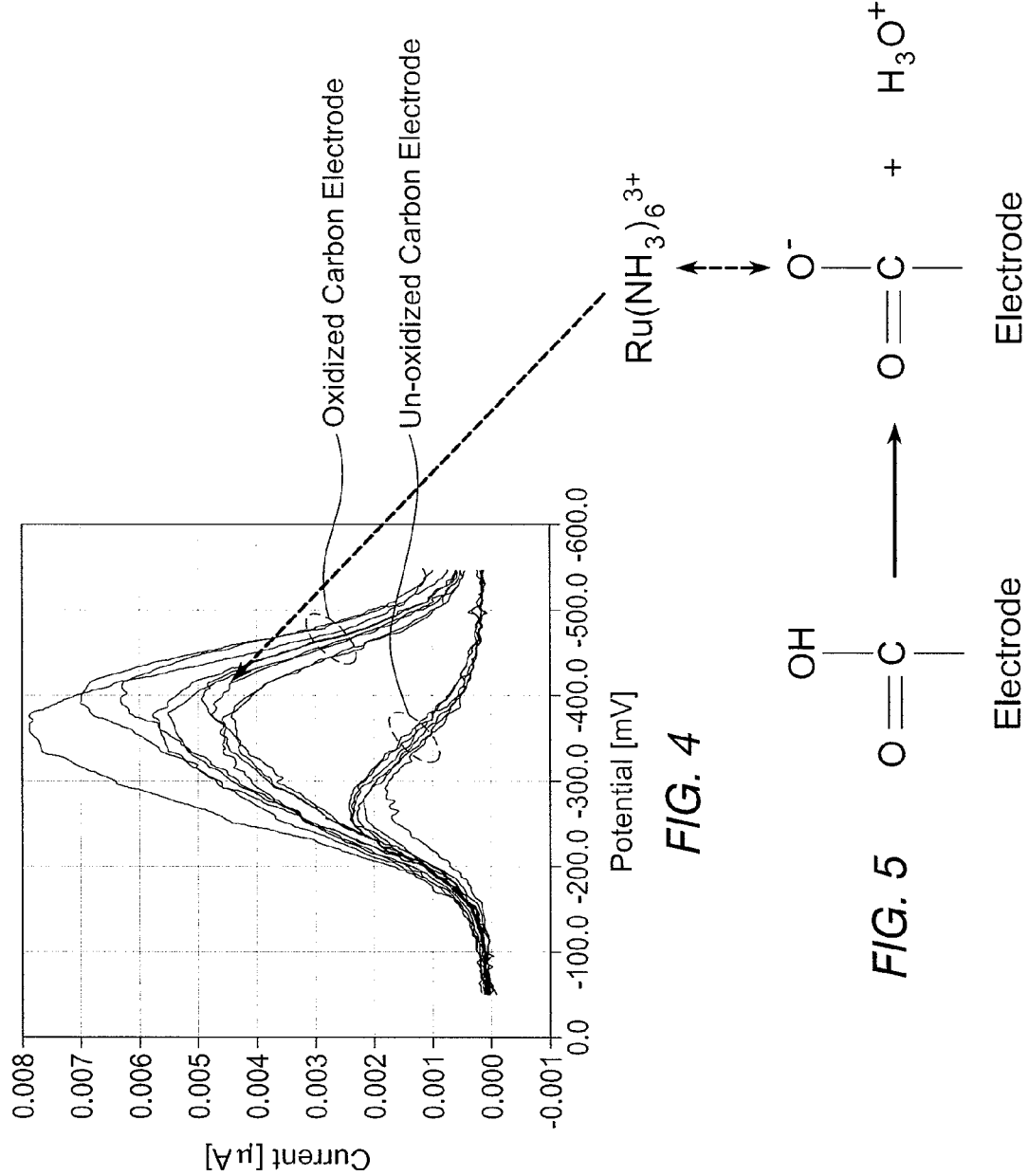

CARBON ELECTRODE SURFACE FOR ATTACHMENT OF DNA AND PROTEIN MOLECULES

RELATED APPLICATIONS

This application claims priority to U.S. Provisional Application Nos. 60/530,065; filed Dec. 15, 2003; and 60/620,374; filed Oct. 20, 2004; both of which are incorporated herein by reference in their entirety.

BACKGROUND OF THE INVENTION

1. Field of the Invention

This invention relates to modification of electrode surfaces to enhance attachment of nucleic acids and proteins. More particularly, the invention relates to methods for making and preparing such electrodes for use in the detection of nucleic acid hybridization.

2. Description of the Related Art

One method to detect the presence of a target nucleic acid sequence in a sample is to immobilize a probe nucleic acid sequence that is complementary to the target sequence on or near the surface of an electrode. If the target nucleic acid sequence is present and conditions are favorable, the target sequence will hybridize with the complementary probe sequence. The electrochemical characteristics of the electrode will then be altered, allowing electrochemical detection of the hybridization of the target and probe nucleic acids.

Electrochemical detection of nucleic acid hybridization can be aided by the presence of a redox active species. For example, a redox active counterion to the probe and target nucleic acids can be used. The concentration of the redox active counterion near the electrode surface will be higher when the nucleic acids are hybridized as compared to when hybridization is not present. This increase in concentration will be reflected in the electrochemical response to the oxidation or reduction of the redox active counterion. Such an electrochemical quantitation technique is described in A. B. Steel et al., *Electrochemical Quantitation of DNA Immobilized on Gold*, Anal. Chem. 70:4670-77 (1998), hereby expressly incorporated by reference in its entirety. In this publication, Steel et al. describe the use of cobalt (III) trisbipyridyl and ruthenium (III) hexaamine as species which interact with surface-immobilized DNA.

Current methods of electrode fabrication result in background signals that interfere with accurate detection of nucleic acid hybridization in the presence of redox active species. Therefore, there is an unmet need for electrodes and systems that provide more accurate and precise detection of nucleic acid hybridization.

SUMMARY OF THE INVENTION

One aspect of the present invention is a method for making an array of sensors, including providing a fabricated array of electrodes and attaching a probe molecule to at least one of the electrodes utilizing a chemical species that was formed on the electrode's surface during fabrication.

Another aspect of the present invention is a method for conducting an assay of a sample, including: fabricating an electrode; attaching a probe molecule to the electrode by utilizing a chemical species on the electrode's surface that is formed during the fabricating step; and contacting the probe molecule with the sample.

A further aspect of the present invention is a method of detecting polynucleotide hybridization, including: providing a carbon electrode fabricated using a subtractive processing technique that causes formation of carboxylic groups on the electrode; attaching a probe polynucleotide to the electrode using the carboxylic groups, such that upon contacting the probe with a sample potentially containing a target polynucleotide capable of hybridizing with the probe, hybridization may be electrochemically detected.

Another aspect of the present invention is a method of attaching a biomolecule to a surface comprising: providing a surface comprising carbon; exposing the surface to an alkaline solution; treating the surface with EDC or DCC and NHS to form a surface bound intermediate moiety; and contacting the intermediate moiety with the biomolecule to effect attachment of the biomolecule to the surface.

BRIEF DESCRIPTION OF THE DRAWINGS

FIG. 4 shows a square-wave voltammogram of oxidized and unoxidized carbon electrodes in the presence of 5 µM ruthenium (III) hexaamine.

FIG. 5 illustrates the interaction between carboxylic acid groups on the surface of the carbon electrode and ruthenium (III) hexaamine.

DETAILED DESCRIPTION OF THE PREFERRED EMBODIMENT

Some embodiments of the present invention relate to methods for analyzing a nucleic acid. In some preferred embodiments, the nucleic acid comprises DNA. However, references to DNA are not intended to imply that other nucleic acids or nucleic acid analogs (e.g., RNA, PNA) cannot be used in practicing the present invention, except as so required in the claims.

Ruthenium-based counterions are particularly advantageous in quantitating polynucleotides for the purpose of detecting hybridization. Ruthenium amperometry and the use of the complexes $Ru(NH_3)_6^{3+}$ and $Ru(NH_3)_5pyridine^{3+}$ for this purpose are disclosed in U.S. Pat. Application No. 60/424,656, filed Nov. 6, 2002; U.S. patent application Ser. No. 10/424,542 filed Apr. 24, 2003 now abandoned; and U.S. patent application Ser. No. 10/429,291 filed May 2, 2003 issued as U.S. Pat. No. 7,258,978, all of which are hereby incorporated by reference in their entirety.

Electrode materials used for the detection of nucleic acid hybridization may be gold, carbon, or some other conductive material. Carbon electrodes have an advantage over gold in that the reduction of $Ru(NH_3)_6^{3+}$ at a carbon electrode does not overlap with the reduction potential of diatomic oxygen as discussed in the aforementioned U.S. patent application Ser. No. 10/429,291.

Figure 1A:
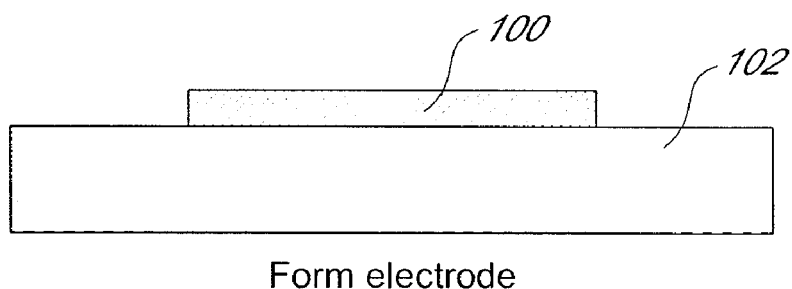
FIGS. 1A and 1B illustrate additive processing techniques in electrode fabrication. The electrode material is placed on a substrate (A) followed by selective deposition of a dielectric layer (B).
Figure 1B:
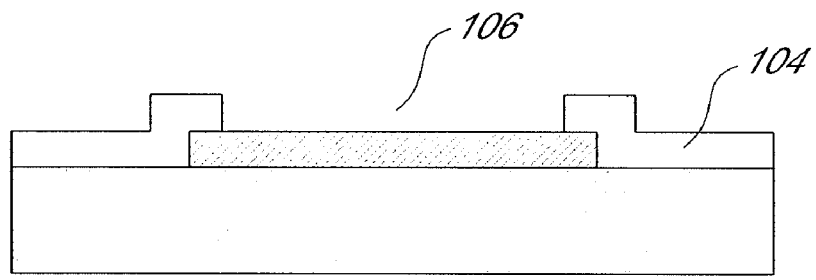

It is desirable that the electrode be microfabricated such that micro arrays of electrodes can be formed. Microfabrication processing techniques known in the prior art are either additive or subtractive. In additive processing, the electrode material 100 is placed on a dielectric substrate 102 as illustrated in FIG. 1A. FIG. 1B shows that a dielectric layer 104 is then selectively deposited on the substrate and electrode such that an area 106 on top of the electrode is left exposed. The selective layering can be accomplished with screen-printing of the dielectric layer followed by UV or thermal curing. Alternatively, the substrate and electrode can be laminated using a pre-drilled overcoat made of a suitable material such as Kapton-brand polyimide film. Additive processing has the drawback that the electrode dimensions cannot be as precisely controlled as they are in subtractive processing.

Figure 2A:
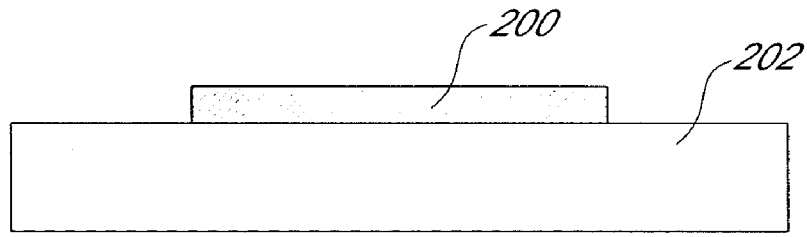
FIGS. 2A-2C illustrate subtractive processing techniques. The electrode material is placed on a substrate (A) followed by laying down of a dielectric layer (B) and finally a removal of an area of the dielectric layer (C).
Figure 2B:
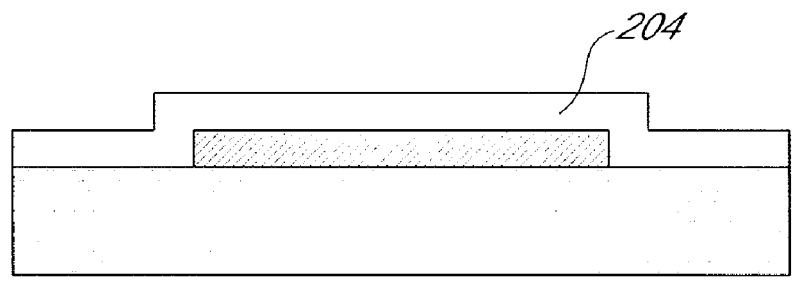
Figure 2C:
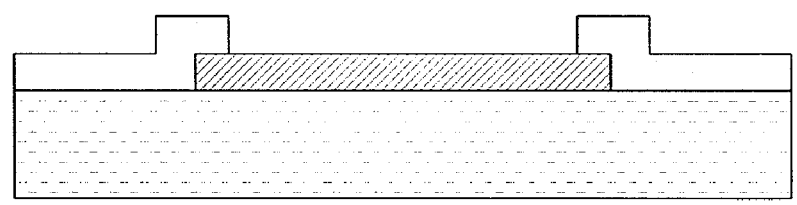

In subtractive processing, the electrode material 200 is placed on a dielectric substrate 202 as illustrated in FIG. 2A. FIG. 2B shows that the electrode material 200 and dielectric substrate is then coated with a dielectric layer 204. Part of the dielectric layer 204 is then selectively removed as shown in FIG. 2C. The removal of the dielectric layer is accomplished by using photolithography or other suitable technique for fabricating circuit boards or semiconductors.

U.S. Pat. No. 5,632,957 discloses a subtractive process whereby a semiconductor is coated with an insulator oxide layer followed by a metal electrode material patterned by a conventional lithographic technique, a glass overcoat, and a nitride layer. The nitride layer and glass overcoat were etched in the region above the patterned electrode exposing the electrode. The electrode was then treated with aminopropylsilene (APS), which adhered to the metal layer and served as an attachment layer for DNA capture probes. U.S. Pat. No. 5,632,957 is hereby incorporated by reference in its entirety.

While it is preferred that the fabrication process produce an array of electrodes, any number of electrodes, including a single electrode, can be created using the present methods. The electrodes can be functionalized such that they can be used in conducting an electrochemical assay of a sample. Preferably, the assay detects whether a target nucleic acid sequence is present. In addition, some assays can also detect the amount of the target present.

One embodiment of the invention provides for the use of photolithography techniques in the electrode manufacture. However, any suitable microfabrication technique known in the art may be used and techniques expressly contemplated include ion beam etching and laser ablation. Such techniques sometimes result in contamination of the electrode surface by the production of various surface functional groups and adsorbed species. Some embodiments of the present invention make use of the produced surface functional groups to attach a nucleic acid, protein, and other molecule to the electrode.

Figure 3A:
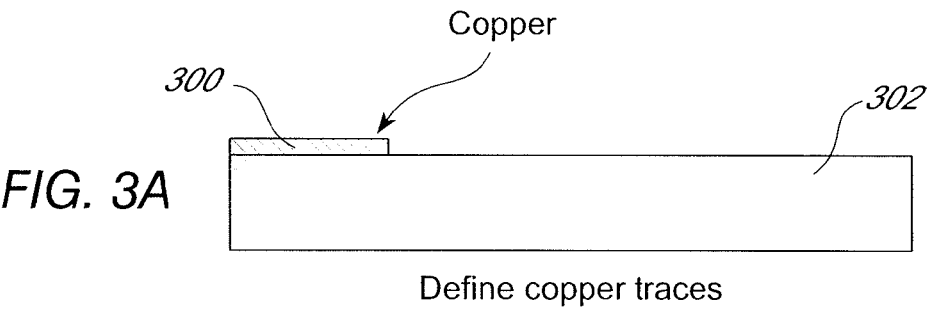
FIGS. 3A-3D illustrate an electrode fabrication process.

In some preferred embodiments, the electrode material includes carbon. Advantageously, the electrode can be glassy carbon, carbon fiber, graphite, carbon paste, or any conductive carbon ink. However, any other conductive material such as a metal, conductive polymer, or composite may be used. FIGS. 3A-3D illustrate one example of an electrode manufacturing process. The process starts with a substrate having a laminated copper foil. For example, the substrate may be a fiberglass substrate such as FR-4. In FIG. 3A, copper traces 300 are defined on the substrate 302. The copper traces 300 may be defined by first coating the copper laminate with a photoresist compound via dipping, spraying, rolling, laminating, or any other procedure known to those skilled in the art. The desired locations for the copper traces 300 are then defined photolithographically on the photoresist. The unexposed regions of the photoresist are removed, such as by using an alkaline solution. Copper etching removes the copper exposed by the removed photoresist. Any procedures known or readily apparent to those skilled in the art may be used to remove the photoresist and to etch the copper. Finally, the remaining photoresist is removed using a strong alkaline solution, organic solvent, or other technique known or readily apparent to those skilled in the art.

Figure 3B:
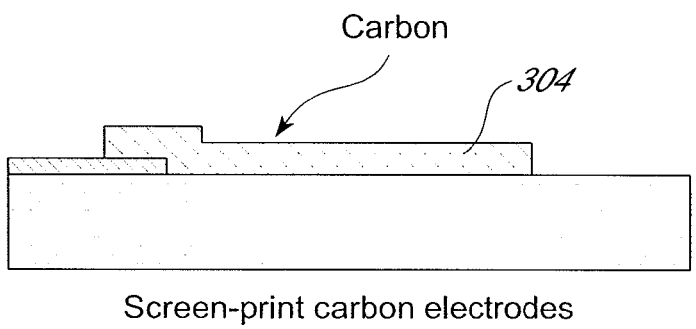
Figure 3C:
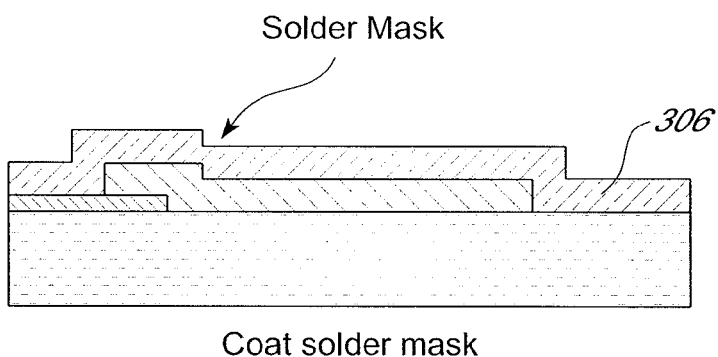

As shown in FIG. 3B, an array of carbon electrodes 304 can be screen-printed on the substrate 302 such that the carbon electrodes 304 are electrically connected to the copper traces 300. Any procedure known to those skilled in the art may also be used to deposit the electrode material 304 unto the substrate 302 and copper traces 300. Preferably, the electrode material 304 is in direct contact with the copper traces 300. Alternatively, an additional conductive material may be used to make the electrical connection between the electrode 304 and the copper traces 300. In FIG. 3C, a dielectric layer 306 is coated on the substrate 302, carbon electrodes 304, and copper traces 300. In some advantageous embodiments, the dielectric layer is a liquid photoimageable (LPI) solder mask.

In some embodiments, portions of the substrate 302 and copper traces 300 can be photolithographically coated with a solder mask prior to carbon electrode screen printing. In general, solder mask processing includes coating with a solder mask, curing the mask, photolithographically defining regions, developing the mask, and finally curing again.

Figure 3D:
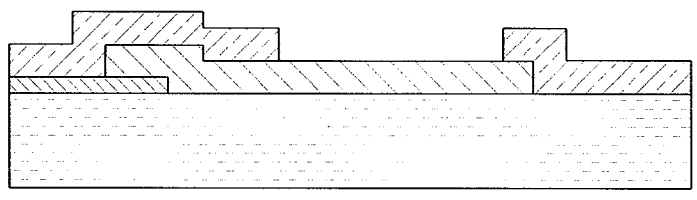

The final fabrication step is illustrated in FIG. 3D. If a LPI solder mask is used, areas of the solder mask 306 above the carbon electrodes 304 are photolithographically defined. Developing the solder mask 306 exposes the carbon electrodes 304. Alternatively, the dielectric layer 306 may be defined by first coating it with a mask layer such as photoresist. Areas above the carbon electrodes 304 are then photolithographically defined on the mask layer, followed by removal of the unexposed mask and etching of the dielectric layer 306. Whatever procedure is used, the resulting electrode array structure leaves the carbon surface of the electrodes 304 exposed while protecting the copper traces 300 and substrate 302 from exposure to a sample. An advantage of the present invention is that by using photolithography to define the copper traces 300 and the area of the dielectric layer 306 that is removed, the electrode dimensions can be precisely controlled.

Although FIGS. 3A-3D illustrate one preferred microfabrication process, other fabrication processes known to those skilled in the art may be used.

It has now been discovered that in this type of microfabrication technique, developing of the solder mask oxidizes the exposed carbon surfaces, producing contaminating surface species such as carboxylic acid groups. These carboxylic acid groups alter the electrochemical characteristics of the electrode. Furthermore, the carboxylic acid groups may interact with species in solution.

The voltammograms in FIG. 4 illustrate the effect of surface carboxylic acid groups on the reduction of $Ru(NH_3)_6^{3+}$. The analyte solution for the voltammograms contained 5 μM ruthenium (III) hexaamine, tris buffer, and NaCl as the supporting electrolyte. The reference electrode was Ag/AgCl. The concentration of chloride in solution was 10 mM. As shown in the voltammograms, when the carbon surface contains carboxylic acid groups, the reduction of $Ru(NH_3)_6^{3+}$ produces higher currents with peaks at more negative potentials than when an un-oxidized carbon surface is used. Thus, the oxidized carbon surface produces a higher background signal, which can interfere with measurements of nucleic acid hybridization. The higher current is due to the attraction between negatively charged de-protonated carboxylic groups and positively charged $Ru(NH_3)_6^{3+}$ as illustrated in FIG. 5. Such attraction can result in adsorbed $Ru(NH_3)_6^{3+}$ species and an increase in the concentration of $Ru(NH_3)_6^{3+}$ near the electrode surface relative to the bulk solution concentration.

Thus, an increase is observed in the detected charge transfer between $Ru(NH_3)_6^{3+}$ and the electrode during reduction of $Ru(NH_3)_6^{3+}$.

One approach to solve this problem could be to avoid electrode contamination by using additive microfabrication techniques. Some embodiments of the present invention, however, allow subtractive techniques to be used instead, or in addition to, additive techniques. Thus, the dimensional control afforded by subtractive techniques can be realized. Further, some embodiments of the present invention utilize the contaminated surface to provide functional groups that can be used to attach nucleic acids, proteins, and other molecules to the electrode surface. Attachment of molecules to an electrode surface following photolithographic or other microfabrication techniques may be done using any surface functional groups or adsorbed species naturally produced as a result of the fabrication process. In some preferred embodiments, carboxylic acid groups are utilized.

Some advantageous embodiments make use of carboxylic acid groups on a carbon electrode surface to attach nucleic acid probe sequences to the electrode that are complementary to a nucleic acid sequence of interest. In some embodiments, the probe sequence is attached directly to the electrode surface via a chemically reactive linker group that is attached to the probe sequence. The linker group may be such that it will react directly with the carboxylic acid or other group on the carbon electrode surface. Alternatively, the surface group is first converted to another chemical species that is suited for reaction with the linker group.

Preferably, proteins such as avidin or other linkers are attached to the electrode surface utilizing the surface functional groups. Avidin can then facilitate attachment to the electrode of a probe nucleic acid sequence that is functionalized with a biotin moiety via the non-covalent interaction between avidin and biotin. The attachment of proteins to the electrode surface may be accomplished by direct reaction between surface functional groups and appropriate reactive groups on the protein. Alternatively, the surface functional groups are first converted to another chemical species prior to attachment of the protein. The attached protein layer should be sufficiently porous to allow ions in a liquid solution to pass from the bulk solution to the electrode surface.

The use of proteins such as avidin or other linkers may be advantageous in certain embodiments. In these embodiments, the use of protein linkers provides additional flexibility in the use of the electrode and the surface; enabling the replacement of a probe nucleic acid sequence with a different probe nucleic sequence. For example, where a probe nucleic acid sequence is attached to the electrode via interaction between avidin that is bound to the electrode and biotin that is bound to the nucleic acid, the biotinylated nucleic acid may be removed and replaced with a different biotinylated nucleic acid, thereby allowing use of the same functionalized electrode surface for different nucleic acid assays. Additionally, this embodiment would be advantageous in any other circumstances where covalent binding of the nucleic acid is not desirable.

Functional groups formed on oxidized carbon have previously been used to attach nucleic acids to a carbon surface. Chemistries such as those used for attachment in the prior art can also be used in the present invention. However, these prior art procedures have required electrochemical or chemical pre-treatment of the carbon in order to form the surface species as opposed to the present invention, where at least in one embodiment, the attachment groups are generated due to the fabrication method. For example, U.S. Pat. No. 5,312,527 describes electrochemically generating carboxylic acid groups on a carbon electrode followed by treatment with 1-(3-dimethylaminopropyl)-3-ethyl-carbodiimide and sodium N-hydroxysulfosuccinimide, leaving N-hydroxysulfosuccinimide esters of the carboxylic acid groups on the electrode surface. Polynucleotide probes were then reacted with the activated carbon surface leading to attachment of the probes to the electrode. A similar procedure is described in U.S. Pat. No. 6,221,586. Alternatively, U.S. Pat. No. 6,207,369 discloses oxidizing carbon fibril composite electrodes in a chromic acid solution. The oxidized electrodes were then reacted with 1-ethyl-3-(3-dimethylaminopropyl)-carbodiimide (EDC) or N,N'-dicyclohexyl-carbodiimide (DCC) and N-hydroxysuccinamide (NHS). Reaction of the activated electrodes with streptavidin effected immobilization of the streptavidin unto the electrodes. Treatment with a biotin labeled oligonucleotide resulted in the binding of the biotin moiety with the streptavidin and hence, immobilization of the oligonucleotide on the electrode. U.S. Pat. No. 6,180,356 discloses electropolymerization of a ruthenium containing thin film unto the surface of a carbon electrode. The thin film contained surface carboxyl groups, which were reacted with EDC or DCC and NHS. Probe DNA containing an amine linker was immobilized by reaction with the treated electrode. U.S. Pat. Nos. 5,312,527; 6,221,586; 6,207,369; and 6,180,356 are hereby incorporated by reference in their entirety.

By utilizing the functional groups or adsorbed species naturally formed on the surface of the electrode by the fabrication process for attachment of desired moieties, some embodiments of the present invention avoid the problems associated with contamination. At the same time, some embodiments of the invention remove the necessity of separately activating the carbon surface electrochemically or chemically prior to nucleic acid attachment.

Figure 6:
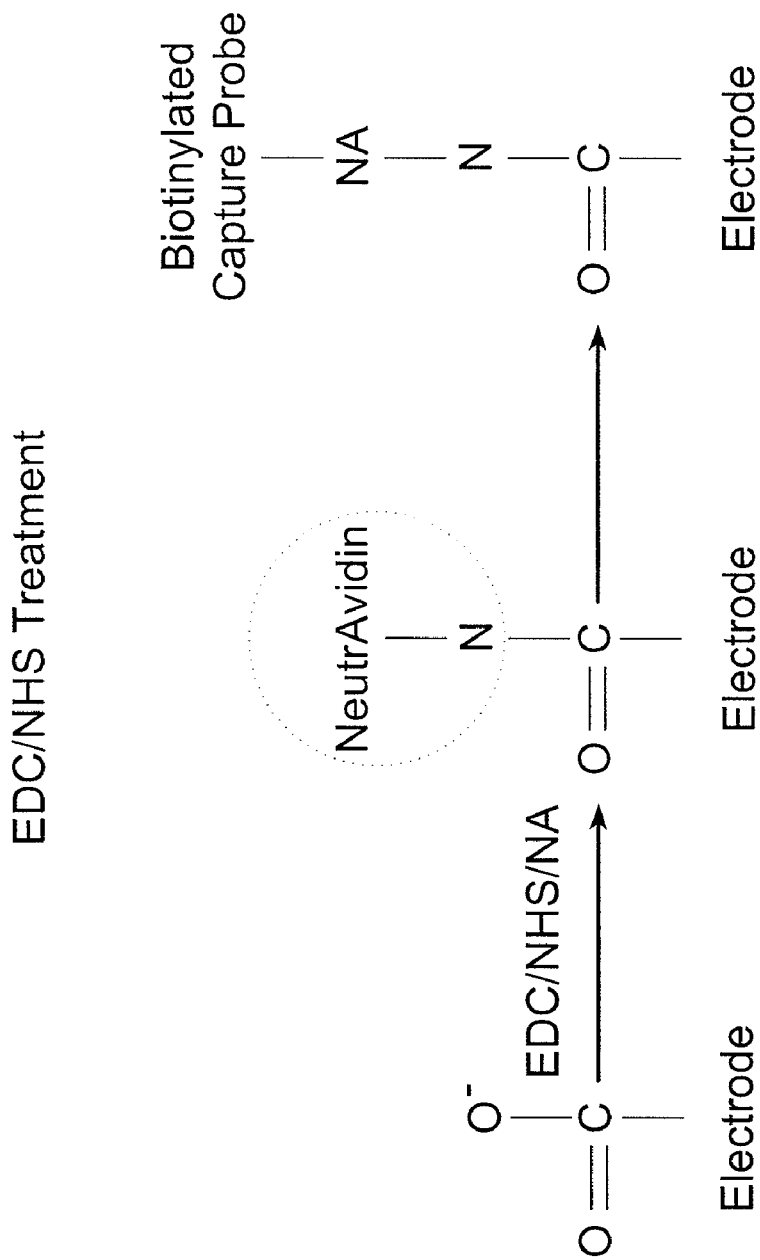
FIG. 6 illustrates immobilization of a DNA probe onto a carbon electrode.

One preferred embodiment is illustrated in FIG. 6. After microfabrication of the carbon electrode array using lithography, carboxylic acid groups on the oxidized carbon electrode surface are converted to NHS esters by treatment with a carboiimide, such as EDC or DCC, and NHS. The NHS ester groups are then reacted with an avidin molecule, which results in the attachment of the avidin to the carbon electrode surface. Biotinylated DNA capture probes are then attached to the electrode via binding between avidin and biotin. The resulting electrode can be used to detect hybridization between the DNA capture probes and complementary target DNA in a sample solution.

In the above procedure, the electrode may be cleaned, when necessary, with a saline solution such as PBS saline. The avidin protein can be provided in a buffer solution such as a phosphate buffer. Unreacted NHS esters can be deactivated with a sodium phosphate solution. The biotinylated probes can be provided in a Tris/LiCl solution. It may be desirable to use a protein stabilizing reagent such as StabilCoat™.

As used herein "avidin" refers to a biotin-binding protein, which includes, among others, the glycoprotein avidin; the non-glycosylated streptavidin protein; proteins processed to remove the carbohydrate, such as NEUTRAVIDIN® available from Molecular Probes; and proteins that have selective nitration of tyrosine residues in the biotin binding sites, such as CAPTAVIDIN™ available from Molecular Probes.

Preferably, detection is aided by the inclusion of a reducible ionic species, such as $Ru(NH_3)_6^{3+}$ in the sample solution. Reduction of $Ru(NH_3)_6^{3+}$ to $Ru(NH_3)_6^{2+}$ can be detected by amperometry or some other electrochemical technique. The reduction current will be greater when the probe DNA is hybridized with the target DNA than when the probe DNA is unhybridized. This increase in reduction current is due to increase in the concentration of $Ru(NH_3)_6^{3+}$ near the electrode surface upon DNA hybridization. Positively charged $Ru(NH_3)_6^{3+}$ is attracted to the negatively charged phosphate backbone of the DNA. When the DNA is hybridized, more negatively charged phosphate backbone will be near the electrode resulting in more attracted $Ru(NH_3)_6^{3+}$. Those skilled in the art will recognize that any suitable redox active counterion or combination of counterions may be substituted for $Ru(NH_3)_6^{3+}$, such as $Ru(NH_3)_5pyridine^{3+}$, other ruthenium complexes, or other reducible ionic species.

The target DNA may be contacted with the probe via any suitable manner known to those skilled in the art. Preferably, the number of target molecules exceeds the number of probe molecules in order to maximize the opportunity of each probe DNA molecule to hybridize with a target DNA molecule. If a target DNA sequence is complementary to the probe sequence, the molecules can hybridize. Whether or not hybridization actually takes place may be influenced by various stringency factors such as temperature, pH, or the presence of a species able to denature various hybridized molecules. Therefore, it may be desirable to adjust the assay conditions to achieve a suitable level of stringency. Maximum stringency would be a condition in which perfectly complementary DNA molecules may hybridize, while all others do not. Ideal conditions will generally be those which strike a balance between minimizing the number of hybridizations between noncomplementary molecules (false positives) and minimizing the number of probes which remain unhybridized despite the presence of eligible complementary target molecules (false negatives). Increasing the quantity and/or size of target DNA molecules are examples of techniques that can be useful in minimizing false negatives.

While any suitable electrochemical technique may be used, amperometry is a preferred technique. The current measured during amperometric detection can be correlated with the amount of $Ru(NH_3)_6^{3+}$ near the electrode surface, which can in turn be correlated to the quantity of phosphate groups on the backbones of the probe and target DNA molecules. Quantitation of the DNA phosphate groups permits distinguishing between hybridized and unhybridized DNA and the determination of whether the DNA being probed is complementary to the probe sequence and thus, contains the target of interest.

The measurable distinction between hybridized and unhybridized DNA can be made even more profound by using target DNA that is substantially longer than the probe DNA. The longer probe DNA will accumulate substantially more $Ru(NH_3)_6^{3+}$. Thus, if the probe is hybridized to the target, the electrochemical response will be enhanced relative to when a shorter target molecule is used. A preferred technique for elongating the target DNA is rolling circle amplification (RCA). Longer target DNA molecules can be made and then introduced to the sample solution. Alternatively, it is possible to increase the length of a target DNA molecule after the strand has hybridized to a probe strand. This second technique is often referred to as "on-chip" amplification. Preferred methods of on-chip amplification are head-to-tail polymerization and RCA. On-chip amplification is discussed in greater detail in copending application Ser. No. 10/429,293 filed May 2, 2003 now abandoned, which is hereby expressly incorporated by reference.

Another technique for increasing the signal contrast between hybridized and unhybridized DNA is to limit the contribution to the measured reduction current of the $Ru(NH_3)_6^{3+}$ that is attracted to the probe molecules. In particular, this can be done by limiting the electrical attraction between the probes and $Ru(NH_3)_6^{3+}$. For example, if the probes are constructed such that they do not contain a negatively charged backbone, then they will not attract counterions. Accordingly, more of the detectable signal will be due to counterions associated with the target DNA. In cases where hybridization has not occurred, the detectable signal will be measurably lower since the target molecules are not present to participate in counterion attraction.

Probes without a negatively charged backbone can include peptide nucleic acids (PNAs), phosphotriesters, methylphosphonates. These nucleic acid analogs are known in the art.

In particular, PNAs are discussed in: Nielsen, "DNA analogues with nonphosphodiester backbones," *Annu Rev Biophys Biomol Struct*, 1995; 24: 167-83; Nielsen et al., "An introduction to peptide nucleic acid," *Curr Issues Mol Biol*, 1999; 1(1-2):89-104; and Ray et al., "Peptide nucleic acid (PNA): its medical and biotechnical applications and promise for the future," *FASEB J.*, 2000 Jun.; 14(9):1041-60; all of which are hereby expressly incorporated by reference in their entirety.

Phophotriesters are discussed in: Sung et al., "Synthesis of the human insulin gene. Part II. Further improvements in the modified phosphotriester method and the synthesis of seventeen deoxyribooligonucleotide fragments constituting human insulin chains B and mini-CDNA," *Nucleic Acids Res*, 1979 Dec. 20; 7(8):2199-212; van Boom et al., *Nucleic Acids Res*, 1977 Mar.; 4(3):747-59; and Marcus-Sekura et al., "Comparative inhibition of chloramphenicol acetyltransferase gene expression by antisense oligonucleotide analogues having alkyl phosphotriester, methylphosphonate and phosphorothioate linkages," *Nucleic Acids Res*, 1987 Jul. 24; 15(14): 5749-63; all of which are hereby expressly incorporated by reference in their entirety.

Methylphosphonates are discussed in: U.S. Pat. No. 4,469,863 (Ts'o et al.); Lin et al., "Use of EDTA derivatization to characterize interactions between oligodeoxyribonucleoside methylphophonates and nucleic acids," *Biochemistry*, 1989, Feb. 7; 28(3):1054-61; Vyazovkina et al., *Nucleic Acids Res*, 1994 Jun. 25; 22(12):2404- 9; Le Bec et al., "Stereospecific Grignard-Activated Solid Phase Synthesis of DNA Methylphosphonate Dimers," *J Org Chem*, 1996 Jan. 26; 61(2): 510-513; Vyazovkina et al., *Nucleic Acids Res*, 1994 Jun. 25; 22(12): 2404-9; Kibler-Herzog et al., "Duplex stabilities of phosphorothioate, methylphosphonate, and RNA analogs of two DNA 14- mers, Nucleic Acids Res, 1991 Jun. 11; 19(11): 2979-86; Disney et al., "Targeting a Pneumoeystis" carinii group I intron with methylphosphonate oligonucleotides: backbone charge is not required for binding or reactivity," *Biochemistry*, 2000 Jun. 13 ; 39(23):6991-7000; Ferguson et al., "Application of free-energy decomposition to determine the relative stability of R and S oligodeoxyribonucleotide methyiphosphonates," *Antisense Res Dev,* 1991 Fall; 1(3) :243-54; Thiviyanathan e al., "Structure of hybrid backbone methyiphosphonate DNA heteroduplexes: effect of R and S stereochemistry," *Biochemistry*, 2002 Jan. 22; 41(3):827-38; Reynolds et al., "Synthesis and thermodynamics of oligonucleotides containing chirally pure R(P) methyiphosphonate linkages," *Nucleic Acids Res*, 1996 Nov. 15; 24(22): 4584-91; Hardwidge et al., "Charge neutralization and DNA bending by the *Escherichia coli* catabolite activator protein," *Nucleic Acids Res*, 2002 May 1; 30(9): 1879-85; and Okonogi et al., "Phosphate backbone neutralization increases duplex DNA flexibility: A model for protein binding," *PNAS U.S.A.*, 2002 Apr. 2; 99(7):4156-60; all of which are hereby incorporated by reference.

Alternatively, a probe may be constructed that contains both charged nucleic acids and uncharged nucleic acid analogs. Similarly, pure DNA probes can be used alongside probes containing uncharged analogs in an assay. However, precision in distinguishing between hybridized and unhybridized probe DNA will generally increase according to the electrical charge contrast between the probe and the target. Hence, the exclusive use of probes made entirely of an uncharged nucleic acid analog will generally allow the greatest signal contrast between hybridized and non-hybridized molecules on the chip. In general, probes containing methylphosphonates are preferred. Probes containing phosphotriesters are less preferred since they are generally not soluble in an aqueous medium.

Although the preferred embodiment of the present invention is a method for detecting polynucleotide hybridization, the techniques and methods disclosed herein can also be used to fabricate other electrode based sensors. For example, by attaching probe molecules other than nucleotides to the electrode surface by the invented technique, sensors to detect the presence or amount of a variety of chemical species or physical conditions may be constructed. Such sensors can be used in liquid, solid, or gaseous media. Furthermore, some embodiments of the invention can include the use of any electrode-based technique, including those other than electrochemistry.

What is claimed is:

1. A method for making an array of sensors, comprising:
providing an array of carbon electrodes, each carbon electrode comprising a surface, wherein said surfaces are exposed;
coating the array of carbon electrodes with a dielectric layer such that the dielectric layer covers said surfaces;
selectively removing a portion of the dielectric layer using photolithography to expose a first portion of each of said surfaces, wherein a second portion of each of said surfaces remain coated by the dielectric layer, wherein the selective removal causes formation of a first chemical species on the first portion of said surfaces; and
attaching a probe molecule to at least one of the carbon electrodes utilizing the first chemical species, wherein attaching the probe molecule comprises one or more of the following:
a) directly reacting the probe molecule with the first chemical species,
b) converting the first chemical species to a second chemical species followed by directly reacting the probe molecule with the second chemical species,
c) directly reacting a linker molecule with the first chemical species followed by reacting the probe molecule with the linker molecule, and
d) converting the first chemical species to a second chemical species followed by reacting a linker molecule with the second chemical species and reacting the probe molecule with the linker molecule.

2. The method of claim 1, wherein said array of carbon electrodes comprises a plurality of carbon electrodes positioned on a substrate and electrically connected to a plurality of conductive traces on the substrate.

3. The method of claim 2, wherein coating the array of carbon electrodes comprises coating the carbon electrodes, substrate, and conductive traces with said dielectric layer.

4. The method of claim 1, wherein the dielectric layer comprises a liquid photoimageable solder mask and selectively removing the portion of the dielectric layer comprises photolithographically defining regions on the solder mask and then developing the solder mask.

5. The method of claim 1, wherein selectively removing the portion of the dielectric layer comprises:
coating the dielectric layer with a mask layer;
photolithographically defining regions on the mask layer;
removing the defined regions on the mask layer to expose portions of the dielectric layer; and
etching the exposed portions of the dielectric layer to expose the first portion of the carbon electrode surfaces.

6. The method of claim 1 wherein the first chemical species that is formed on the first portion of the carbon electrode surfaces is a carboxylic group.

7. The method of claim 6 wherein, converting the first chemical species to the second chemical species comprises reacting the carboxylic group with 1-ethyl-3-(3-dimethylaminopropyl)-carbodiimide or N,N'-dicyclohexyl-carbodiimide and reacting the species formed thereby with N-hydroxysuccinamide.

8. The method of claim 7, wherein the linker molecule is a protein and reacting the linker molecule with the second chemical species comprises reacting the species formed by the N-hydroxysuccinamide with the protein.

9. The method of claim 8 wherein the protein comprises an avidin.

10. The method of claim 9 wherein the probe molecule comprises a biotin moiety and attaching the probe molecule comprises binding the biotin moiety to the avidin.

11. The method of claim 1 wherein the probe molecule comprises a nucleic acid.

12. The method of claim 1 wherein the dielectric layer is a liquid photoimageable solder mask.

13. The method of claim 12 wherein selectively removing a portion of the dielectric layer comprises photolithographically defining areas above the carbon electrodes and developing the liquid photoimageable solder mask using an alkaline solution.

14. The method of claim 13 wherein use of the alkaline solution causes formation of the first chemical species on the first portion of the electrode surfaces.

15. A method of conducting an assay of a sample comprising:
making an array of sensors using the method of claim 1; and
contacting the probe molecule with the sample.

16. The method of claim 15 further comprising the step of assaying the sample using an electrochemical technique.

17. The method of claim 16 wherein the electrochemical technique is amperometry.

18. The method of claim 16 further comprising the step of contacting the probe molecule with a species capable of electron transfer with the electrode.

19. The method of claim 18 wherein the species capable of electron transfer comprises ruthenium.

20. The method of claim 15 wherein the sample comprises a target molecule.

21. The method of claim 20 wherein the assay detects whether the target molecule has hybridized to the probe molecule.

22. The method of claim 21 wherein the target molecule comprises a target molecule nucleic acid sequence and the probe molecule comprises a probe molecule nucleic acid sequence.

23. The method of claim 22 wherein at least a portion of the probe molecule nucleic acid sequence and at least a portion of the target molecule nucleic acid sequence are complementary.

24. The method of claim 1, wherein attaching the probe molecule comprises converting the first chemical species to a second chemical species followed by reacting a linker molecule with the second chemical species and reacting the probe molecule with the linker molecule.

25. The method of claim 1, wherein the array of carbon electrodes is a microarray.

* * * * *